(12) United States Patent
Patel et al.

(10) Patent No.: US 11,317,929 B2
(45) Date of Patent: May 3, 2022

(54) NAVIGATIONAL DEVICE TO GUIDE PLACEMENT OF SPINAL SCREW

(71) Applicant: VANTARI MEDICAL LLC, Timonium, MD (US)

(72) Inventors: Amit R. Patel, Lutherville-Timonium, MD (US); Alex Frederick Hess, Oviedo, FL (US)

(73) Assignee: VANTARI MEDICAL LLC, Timonium, MD (US)

( * ) Notice: Subject to any disclaimer, the term of this patent is extended or adjusted under 35 U.S.C. 154(b) by 0 days.

(21) Appl. No.: 17/291,711

(22) PCT Filed: Dec. 13, 2019

(86) PCT No.: PCT/US2019/066173
§ 371 (c)(1),
(2) Date: May 6, 2021

(87) PCT Pub. No.: WO2020/123911
PCT Pub. Date: Jun. 18, 2020

(65) Prior Publication Data
US 2021/0361298 A1   Nov. 25, 2021

Related U.S. Application Data

(60) Provisional application No. 62/779,122, filed on Dec. 13, 2018.

(51) Int. Cl.
*A61B 17/17* (2006.01)
*A61B 90/11* (2016.01)
(Continued)

(52) U.S. Cl.
CPC .......... *A61B 17/1757* (2013.01); *A61B 90/11* (2016.02); *A61F 2/4455* (2013.01); *A61F 2/4611* (2013.01)

(58) Field of Classification Search
CPC ..... A61B 17/17; A61B 17/1757; A61B 90/11; A61F 2/44; A61F 2/4455; A61F 2/46; A61F 2/4611
See application file for complete search history.

(56) References Cited

U.S. PATENT DOCUMENTS 6,770,074 B2 *  8/2004  Michelson ............. A61F 2/446
                                                                623/17.11
6,949,105 B2     9/2005  Bryan et al.
(Continued)

OTHER PUBLICATIONS

WOSA, PCT/US2019/066173, dated Jan. 30, 2020.
ISR, PCT/US2019/066173, dated Jan. 30, 2020.

*Primary Examiner* — Christopher J Beccia
(74) *Attorney, Agent, or Firm* — Gallet Dreyer & Berkey LLP; Andrew Berks (57) ABSTRACT

A navigational device or jig is provided for accurately guiding the drilling of holes for screws or guidewires for spinal surgery. The jig has a three-point attachment to a vertebra with a jaw that contacts the pars interarticularis and a clip that contacts or attaches to the spinous process. A drill guide support arm moveable laterally with three axes of rotation is provided. The drill guide is a channel that directs a drill bit to a desired location and trajectory. The holes created with the drill bit in a vertebra are used for the insertion of screws or guidewires for any of various procedures requiring screws implanted in a vertebra. In particular, the inventive jig is useful for the precise placement and control of drilled holes for cortical bone trajectory screw placement.

20 Claims, 7 Drawing Sheets

(51) Int. Cl.
*A61F 2/44* (2006.01)
*A61F 2/46* (2006.01)

(56) References Cited

U.S. PATENT DOCUMENTS

| | | | |
|---|---|---|---|
| 8,323,295 B2 * | 12/2012 | Hufner | A61B 17/1757 |
| | | | 606/105 |
| 10,610,380 B2 * | 4/2020 | Abdou | A61B 17/7032 |
| 11,000,312 B2 * | 5/2021 | Thommen | A61B 1/00135 |
| 2002/0077641 A1 | 6/2002 | Michelson | |
| 2018/0008253 A1 | 1/2018 | Thommen et al. | |
| 2018/0235777 A1 | 8/2018 | Abdou | |

\* cited by examiner

NAVIGATIONAL DEVICE TO GUIDE PLACEMENT OF SPINAL SCREW

CROSS REFERENCE TO RELATED APPLICATIONS

This patent application claims priority to PCT Application No. PCT/US19/66173 filed Dec. 13, 2019, which claims priority to U.S. Provisional Patent Application No. 62/779,122 filed Dec. 13, 2018.

FIELD OF THE INVENTION

This invention pertains to an apparatus and method of guiding a drill bit for the insertion of screws or guidewires in spinal fusion surgery with a modular, three-point fixated, reusable navigational device, useful for increasing the safety and precision of drilling holes for spine surgery, particularly for cortical screws.

BACKGROUND

Several techniques and systems are known for correcting and stabilizing bones, including the bones of the spine.[1] Stabilization of the spine for various conditions, such as degenerative disk disease, scoliosis, spondylolisthesis, and spinal stenosis, by way of example, often require attaching implants to the spine and then securing the implants to spinal rods. Such spinal fixation devices can immobilize the vertebrae of the spine and can alter the alignment of the spine over several vertebrae by connecting at least one elongate rod to the sequence of selected vertebrae.

[1] See generally, US Patent Publication US20180000526, published Jan. 4, 2018.

Since the 1950's, pedicle screw and rod constructs have been the gold standard for instrumented lumbar fusions.[2] Fixation through the pedicle allows significant control of the entire vertebral body, and it reduces the rate of nonunion following fusion. Pedicle screws are traditionally inserted at the junction of the lateral facet and transverse process and are directed in a lateral-to-medial trajectory through the pedicle and into the vertebral body.

[2] Shepherd, Daniel L. et al. "The Cortical Bone Trajectory for Lumbar Spine Fusion," Operative Techniques in Orthopaedics, 2017, 27(4) 269-274 https://doi.org/10.1053/j.oto.2017.09.011.

Screws such as polyaxial, monoaxial, or uniaxial screws, are frequently used as fasteners in implantation fixation systems. Once these screws are set in a desired position, the screws are securely fixed in that position to minimize or eliminate movement of the vertebra.[3] This is typically accomplished with a fixation system that securely engages the screw.

[3] H. Wang et al. "Biomechanical efficacy of monoaxial or polyaxial pedicle screw and additional screw insertion at the level of fracture, in lumbar burst fracture: An experimental study," Indian J Orthopedics, 2012, 46(4), 395-401, doi: 10.4103/0019-5413.98827: 10.4103/0019-5413.98827.

The current "traditional" pedicle screw trajectory 330 uses a transpedicular path, either following the anatomic axis of the pedicle directed about 22° in the cephalocaudal direction in the sagittal plane (ie, the anatomic trajectory) or instrumented parallel to the superior end plate of the vertebral body in the sagittal plane (i.e., the straight-forward trajectory).[4] Both cortical and trabecular bone are engaged with the traditionally directed trajectory.

[4] Santoni, B. G. et al., "Cortical bone trajectory for lumbar pedicle screws," The Spine Journal, 2009, 9(5), 366-373, doi:10.1016/j.spinee.2008.07.008.

Figure 15:
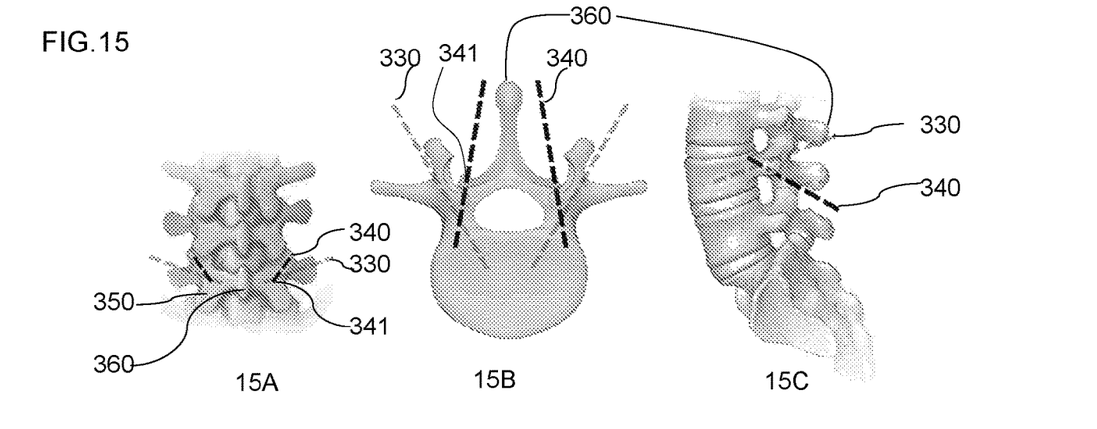
FIG. 15 is a schematic showing various screw trajectories in this invention.

A reemerging modified screw trajectory 340, referred to as "cortical bone trajectory," has been used to treat lumbar spinal instability resulting from conditions such as trauma, spondylolisthesis, tumor, deformity, obesity, rheumatoid arthritis, osteoporosis, or iatrogenic instability.[5,6] The more traditional pedicle screw trajectory and the newer cortical bone trajectory both involve spinal fusion employing screws driven into vertebrae in various configurations that can be used to stabilize the spine, often with the assistance of associated hardware such as rods, plates, and brackets. These configurations are illustrated in FIGS. 15A-C.[7]

[5] See n. 2

[6] Mori, Kanji, et al., "Short-Term Clinical Result of Cortical Bone Trajectory Technique for the Treatment of Degenerative Lumbar Spondylolisthesis with More than 1-Year Follow-Up," Asian Spine J 2016; 10(2):238-244, http://dx.doi.org/10.4184/asj.2016.10.2.238 Asian Spine J 2016; 10(2):238-244

[7] FIG. 15 is taken from note 2.

The new cortical trajectory follows a caudocephalad path sagittally and a laterally directed path in the transverse plane, engaging mostly, if not only, cortical bone in the pedicle with minimal if any involvement of the vertebral body trabecular bone.[8] The theoretical advantage associated with this modified technique is increased cortical bone contact, providing enhanced screw purchase and interface strength independent of trabecular bone mineral density (BMD).

[8] note 4

A new screw design that is shorter and smaller in diameter than the traditional trajectory pedicle screw has been proposed that seeks to maximize the thread contact with this higher density bone surface.[4] It is hypothesized that this increase in cortical bone interference will directly relate to greater holding screw strength, and, thus, less opportunity for loosening.

An additional advantage to the cortical screw trajectory is that the wound to access surgical site can be smaller. With the traditional pedicle screw placement, the lateral-to-medial trajectory of the screw dictates a much wider dissection than the medial-to-lateral trajectory of the newer cortical screw trajectory. A smaller, narrower wound is desirable in surgery and would permit a more rapid recovery and fewer complications.

However, achieving solid implant fixation can be complex clinical challenge for spine surgeons. Progressive construct instability as a result of screw loosening is common complication with pedicle screw instrumentation, especially in patients with poor bone quality. The risk of a pedicle screw loosening is increased with screws that are primarily anchored in trabecular medullary bone and in patients with reduced BMD. Optimizing screw contact with cortical bone may be a method of improving overall screw strength.

Potential problems with existing screw fixation techniques include screw loosening[4] and screw placement.[5] Misplacement of screws may result in dural or neurovascular injury. A review found that screw misplacement ranged from 6%-31% using the freehand technique, 15%-72% with the aid of fluoroscopy, and 0%11% using computed tomography navigation.[9] Moreover, screw placement is somewhat more difficult with the cortical screw trajectory method. Although the cortical screw trajectory has numerous advantages over traditional pedicle screws (minimize dissection, decrease surgical time, stiffer construct, higher pull-out strength to list a few), the main limiting factor hindering wide acceptance and adoption is the technical challenges associated with the cortical trajectory itself. A traditional pedicle screw is simpler to insert as the anatomy is familiar, and the trabecular bone helps guide the instruments and screws in the appropriate position as the tools and implants follow the path of least resistance. On the other hand, the cortical trajectory is not one that follows the path of least resistance. Furthermore, given limited real estate at the point of entry, if the trajectory is not ideal or close to ideal, the path cannot be utilized; the entire construct is typically converted to traditional pedicle screws or the surgeon uses extensive out-riggers and cross-connectors. And lastly, the angulation required is often awkward for surgeons who have trained exclusively with traditional pedicle screws.

[9] Gelalis I D, Paschos N K, Pakos E E, et al, "Accuracy of pedicle screw placement: A systematic review of prospective in vivo studies comparing free hand, fluoroscopy guidance and navigation techniques," Eur Spine J, 2012, 21, 247-255. DOI 10.1007/s00586-011-2011-3

SUMMARY OF THE INVENTION

This invention addresses the problem of screw placement in spinal fusion surgery by providing a navigational device (also termed herein a "jig") for use by a surgeon in spinal surgery adapted to guide the placement of a drill bit for the insertion of screws in the spine of a patient in need of spinal fusion, and in particular lumbar spinal fusion. Accordingly, this invention provides a navigational device or jig with a channel that can be rapidly fixed into a stable position to guide a drill bit in a desired entry point and trajectory. In an embodiment, the inventive jig can be used for either the traditional pedicle screw trajectory or the cortical screw trajectory. This device is useful for increasing the safety and precision of drilling holes in vertebra as compared to conventional freehand techniques.

In an embodiment, this invention provides a device for use by a surgeon in spinal surgery adapted to guide the placement of a drill bit for the insertion of screws in the spine of a patient in need of spinal fusion. In an embodiment, the inventive device provides a chassis having a three-point attachment to a vertebra comprising two mandibles that form a jaw that contacts the pars interarticularis of a vertebra, and a central attachment clip adapted to contact the spinous process of the same vertebra, so that the two jaws and central attachment clip form a stable three-point attachment to the vertebra. In an embodiment, a drill guide support arm comprising a drill guide channel is moveable on the chassis and can move laterally from one side of the chassis to the other and is securable into a desired position. In an embodiment, the guide support arm has three axes of rotation to position the drill guide channel in a desired position and orientation. The drill guide channel determines the trajectory for a drill bit inserted through the guide channel. In an embodiment, the drill guide channel is used to guide a drill bit to drill a hole for a spine screw or guidewire.

In an embodiment, the mandibles that form a jaw that contacts the pars interarticularis of a vertebra may pivot on a transverse axis. In an embodiment, the two mandibles that form a jaw that contacts the pars interarticularis of a vertebra may have a freedom of movement such that the gap in the jaw can expand and contract. In an embodiment, the central attachment clip adapted to contact the spinous process of the same vertebra extends and retracts relative to the chassis.

Figures 12A, 12B:
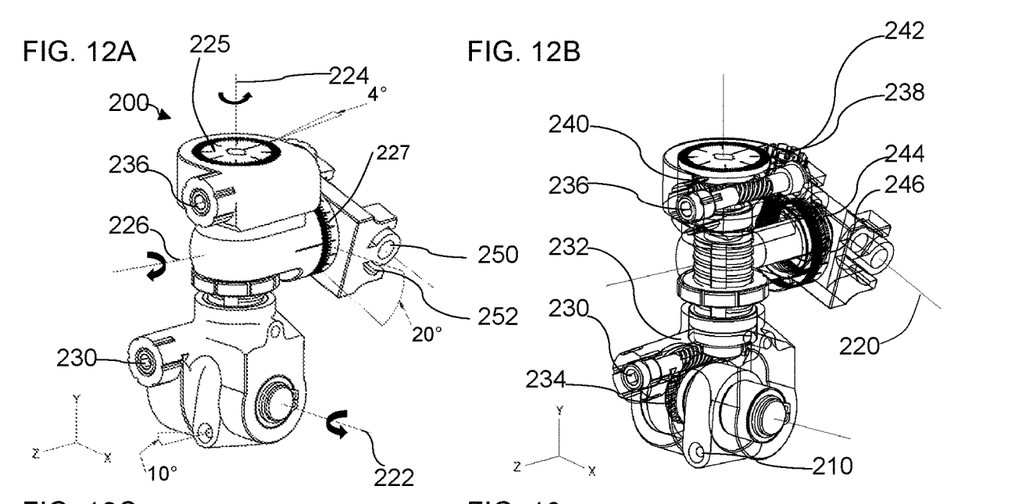
FIG. 12A is a perspective of the guide support arm.
FIG. 12B is a cutaway view showing an embodiment of exemplary internal workings of the guide support arm.

In an alternative embodiment, this invention provides a device for use by a surgeon in spinal surgery adapted to guide the placement of a drill bit for the insertion of screws in the spine of a patient in need of spinal fusion. In an embodiment, the inventive device provides a three-point attachment to a vertebra comprising two mandible arms that form a jaw that contacts the pars interarticularis of a vertebra where screws are to be inserted and a central clip adapted to contact the spinous process of the same vertebra. In an embodiment each mandible arm and the central clip are connected to a chassis, such that the jaw formed by the mandible arms can expand or contract to make a firm connection with the pars interarticularis and the central clip can extend or retract to make a firm connection to the spinous process, such that a stable three-point attachment of the chassis to the vertebra is made. The clip maybe secured to the spinous process by a variety of means: springs, clasps, or guide pins for example. In an embodiment, the chassis, when stabilized in position, is transverse to the spine. In an embodiment, a drill guide support arm comprising a drill guide channel is moveable on a transverse support assembly connected to the chassis and can move transversely on a medio-lateral axis from one side of the transverse support assembly to the other and is securable into a desired lateral position. In an embodiment, the guide support arm may have three perpendicular axes of rotation (i.e., x, y, and z axes as shown in FIG. 12A) to position the drill guide channel in a desired position and orientation, so that a drill bit can be inserted into the drill guide channel and the channel determines the placement and trajectory for the drill bit. In an embodiment, the drill guide channel is used to guide a drill bit to drill a hole for a spine screw or guidewire.

In an embodiment, the transverse support assembly further may include a lateral translational screw on a medio-lateral axis, wherein the lateral translational screw supports the drill guide support arm, and wherein the lateral translational screw can be rotated by a dial to position the drill guide support arm in a desired lateral position.

In an embodiment, the drill guide support arm comprises three worm screws and gears that control the x, y, and z axes of the drill guide support arm.

In an embodiment, the drill guide support arm is detachable from the chassis, and wherein the drill guide support arm is attachable to the chassis. In this way, the jig can be placed with a stable three-point attachment of the chassis to a desired vertebra without the drill guide support arm in position. The absence of the drill guide support arm may make the positioning and attachment of the jig to the vertebra easier for the surgeon. After the chassis is stably attached to a vertebra, the drill guide support arm can be attached to the jig and positioned for the drilling operation.

In an embodiment, the central clip is moveable along a medial axis and can extend or retract on a perpendicular axis to the transverse support assembly. The central clip may be mounted on a medial translational screw threaded through a female fitting in the chassis, and the rotation of the medial translational screw extends or retracts the central clip relative to the position of the transverse support assembly. A knob or dial may be used by the surgeon to rotate the medial translational screw.

In an embodiment, the jaw mandible arms may independently rotate on a transverse axis through a pivot point for each jaw. The jaw mandibles may also rotate on a medial axis in coordination, such that the jaw mandibles move between an expanded and contracted position as required to grip the pars interarticularis. In the illustrated embodiment, the coordinated movement of the jaws between expanded and contracted positions is controlled by a rack and pinion screw, wherein a jaw pinion screw moves an upper and lower rack that are each in communication with a mandible support lever through a pivot joint, such that as the jaw pinion screw rotates, the rack pivots move together or farther apart and the mandible support levers move the mandible on a medial axis to expand or contract the gap at the end of the jaw.

In an embodiment, the drill guide channel is adjusted to a position wherein the drill bit guided by the drill guide channel makes a drilled hole at an entry point medial to the edge of pars interarticularis and directed in a caudal-to-cephalad angle in the sagittal plane and medial-to-lateral in the axial plane.

In an embodiment, the spine screw or guidewire is used for a spinal fusion procedure. The spine screw or guidewire may be used for a spinal fusion procedure. The inventive jig can be used for sacral, lumbar, thoracic, and cervical spine procedures.

In an embodiment, the inventive device may be made from a surgically compatible metal that can be sterilized. The metal may be selected from stainless steel, titanium or a titanium alloy, and tantalum or a tantalum alloy. In an embodiment, the inventive device is intended to be reusable.

In an embodiment, a method is provided of drilling a hole in a vertebra using the device as described above. Also provided is a method of drilling a hole into a vertebra for the placement of a screw or guidewire in a caudal-to-cephalad angle in the sagittal plane and medial-to-lateral in the axial plane where the drill guide channel is adjusted to a position wherein the drill bit guided by the drill guide channel is directed to an entry point medial to the edge of pars interarticularis and directed in a caudal-to-cephalad angle in the sagittal plane and medial-to-lateral in the axial plane, and wherein a hole is drilled by the drill bit. Also provided is a method of drilling a hole into a vertebra for the placement of a screw in a caudal-to-cephalad angle in the sagittal plane and medial-to-lateral in the axial plane, comprising device as described above, wherein a cortical screw is driven into the hole formed by the drill bit. In an embodiment, a guidewire is inserted into the hole formed by the drill bit.

In an embodiment, a method is provided of drilling a hole into a vertebra for the placement of a screw or guidewire in a caudal-to-cephalad angle in the sagittal plane and medial-to-lateral in the axial plane, comprising device as described above, wherein the drill guide channel may be adjusted to drill a second hole on the other side of the spinous process from a first hole.

In an embodiment, a method is provided of drilling a hole into a vertebra for the placement of a screw or guidewire with the device as described above, wherein the three-point attachment of the chassis to a vertebra is fixed without the drill guide arm attached to the chassis or transverse support assembly, and wherein the drill guide arm is then attached to the chassis or transverse support assembly after fixation of the three-point attachment of the chassis.

In an embodiment, a method is provided of drilling a hole into a vertebra for the placement of a screw or guidewire with the device as described above, wherein seven placement parameters are determined in advance, wherein the seven parameters comprise: the gap in the jaw that contacts the pars interarticularis of the vertebra; the extension of spinous process clip from the chassis; the pivot angle of the mandible jaw arms; the medial-lateral translation of the drill guide arm on the chassis; and three degrees of freedom for the drill guide channel on the drill guide arm that allows the barrel to swivel in the x, y, and z planes.

DESCRIPTION OF THE DRAWINGS

FIG. 1 is a top perspective view of apparatus 100. This is the posterior of the apparatus when it is in operation. The cephalad end (pointing towards the head of the patient) is at the bottom as shown in this figure.

FIG. 2 is an alternative top perspective view of apparatus 100.

FIG. 10 is an elevation view of the right side of the apparatus.

FIG. 15A is a posterior view showing the caudocephalad path sagittally and a laterally directed path in the transverse plane screw trajectory and the conventional pedicle screw trajectory. FIG. 15B is a transverse cross section of a spinal vertebra, for example the L5 vertebra. FIG. 15C is a sagittal view of the lumbar section of a spine showing the inventive and convention screw trajectories.

DETAILED DESCRIPTION

Figure 1:
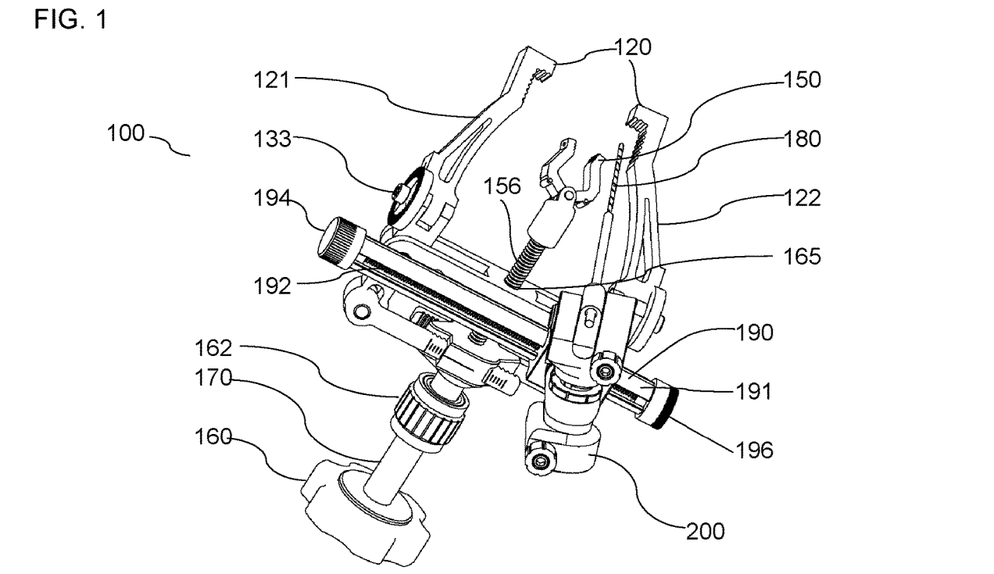
Figure 2A:
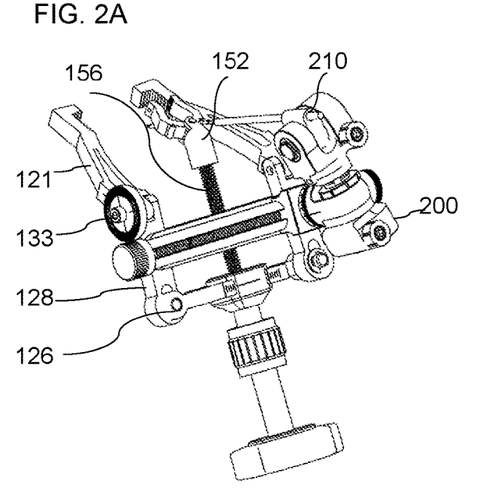
FIG. 2A is a view of the apparatus from the top left.
Figure 2B:
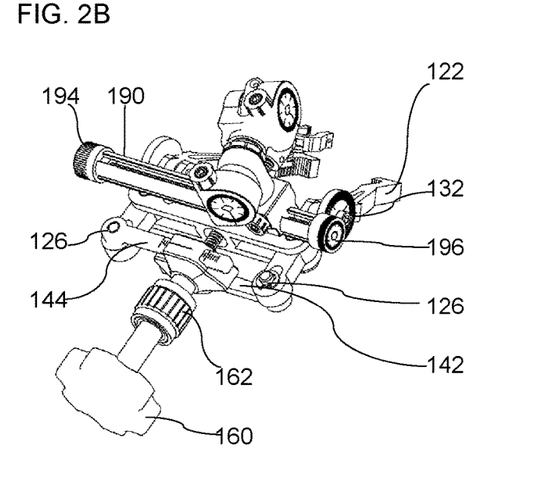
FIG. 2B is a view of the apparatus from the top right.

An embodiment of an inventive navigational device or jig is shown in FIGS. 1-14. The figures show an apparatus 100 for use by a surgeon in spinal surgery adapted to guide the placement of a drill bit for the insertion of screws or guidewires in the spine of a patient in need of spinal fusion or instrumentation. In general, the orientation of 100 as shown in FIG. 1 is that the superior end is at the top of the drawing, and the anterior end is at the bottom. The apparatus 100 will normally be used in a posterior approach to the spine, so the view in FIGS. 1 and 2 are as the surgeon would see 100 in operation. As defined herein, the terms "left," "right," "up," and "down" are relative to the orientation shown in FIGS. 1 and 2A, which is the view as seen by the surgeon. That is, the top or upper end is as shown in these drawings, and right and left are as shown in these drawings. The top of this device is as shown in FIGS. 1 and 2A is pointed towards the caudal (tail) end of the spine.

In an embodiment, this invention provides a device that acts as a jig with a clamp that establishes a three-point attachment to a vertebra, and a guide arm which supports a guide channel, also termed a "barrel," through which a drill bit is inserted. The position and angle of the guide barrel directs a drill bit to a desired location and trajectory.

In an embodiment, five parameters must be established to guide a drill bit correctly for spinal surgery. The guide channel (barrel 210) guiding the drill bit must in an appropriate x, y location on a plane parallel to the vertebra being worked on. This is a function of correct placement of the barrel on the medial and transverse axes of the inventive jig. The drill barrel must also be oriented correctly, meaning the angle determined by three axes of rotation (x, y, and z, FIG. 12A) of the drill guide channel must be correct. This combination of location and orientation is required to correctly establish a desired drill entry point and trajectory for the drill bit.

In an embodiment, this invention provides a device 100 for use by a surgeon in spinal surgery adapted to guide the placement of a drill bit for the insertion of screws or guidewires in the spine of a patient in need of spinal fusion. The apparatus 100 is adapted in particular to guide the placement of screws in a caudo-cephalad path sagittally and a laterally directed path in the transverse plane (340 in FIG. 15), but other screw trajectories are within the scope of this invention, for example trajectory 330, which is a "traditional" pedicle screw trajectory.

In an embodiment, apparatus 100 has a three-point attachment to a vertebra, using two mandibles or legs 121 and 122 that form a jaw 120 that contacts the pars interarticularis (350) of a vertebra and a central attachment point that may be a clip 150 adapted to contact the spinous process (360) of the same vertebra, so that the two jaws and central attachment clip form a three stable three-point attachment to the vertebra. A number of adjustments are required as described in more detail below to establish a stable three-point attachment, due to the natural variability in vertebral configurations.

In an embodiment, a drill guide support arm 200 comprising a drill guide channel 210 (also termed a barrel) is moveable on a transverse assembly 190 and can move transversely on a medio-lateral axis 220 from one side of the transverse assembly to the other and is securable into a desired position. In most figures the drill guide support arm 200 is shown on the right side of assembly 190, but in FIG. 5C the drill guide support arm is shown on the left side of 190, illustrating how the drill guide support arm can move from one end of 190 to the other end.

In an embodiment, the drill guide support arm has three axes of rotation (222, 224, and 226) to position the drill guide channel 210 in a desired orientation, and wherein the channel determines the trajectory for a drill bit 180 inserted through the guide channel. As used herein, the "desired position" is the horizontal position of the drill guide support arm on assembly 190, and the "desired orientation" or "desired trajectory" is the angle of the drill guide channel 210 defined by the three axes of rotation of the drill guide support arm.

In an embodiment, a drill bit 180 inserted in guide channel 210 can be used to precisely drill a hole at a position and trajectory desired by the surgeon, and thereby eliminate risks of a purely freestyle handling of a drill.

Figure 4A:
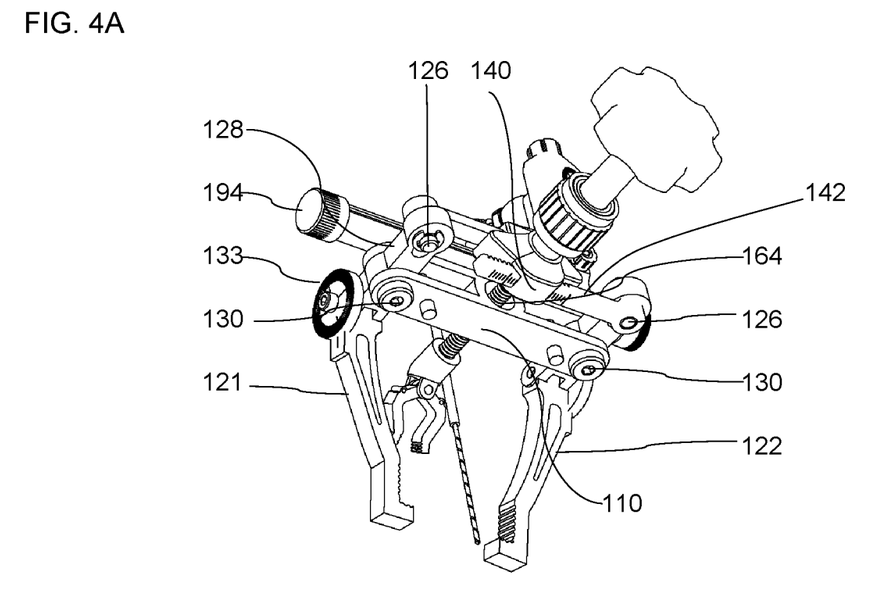
FIG. 4A is a perspective view of apparatus 100 from the bottom, i.e., the anterior side. The cephalad end is the top right in the drawing.
Figure 4B:
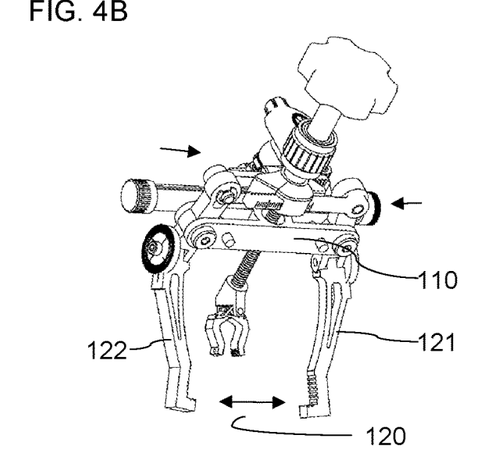
FIG. 4B is the same view, but with the jaw in the expanded position.
Figure 4C:
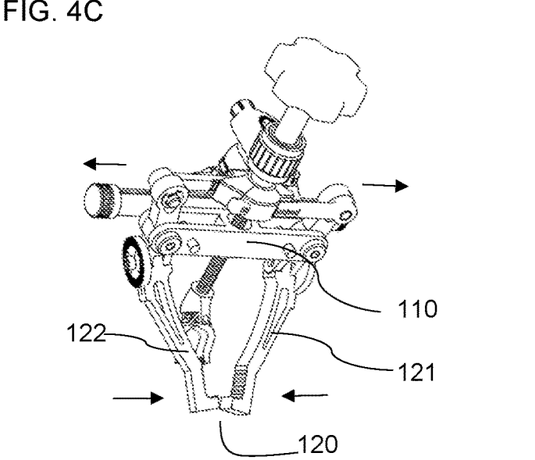
FIG. 4C is the same view with the jaw in the contracted position.
Figure 14:
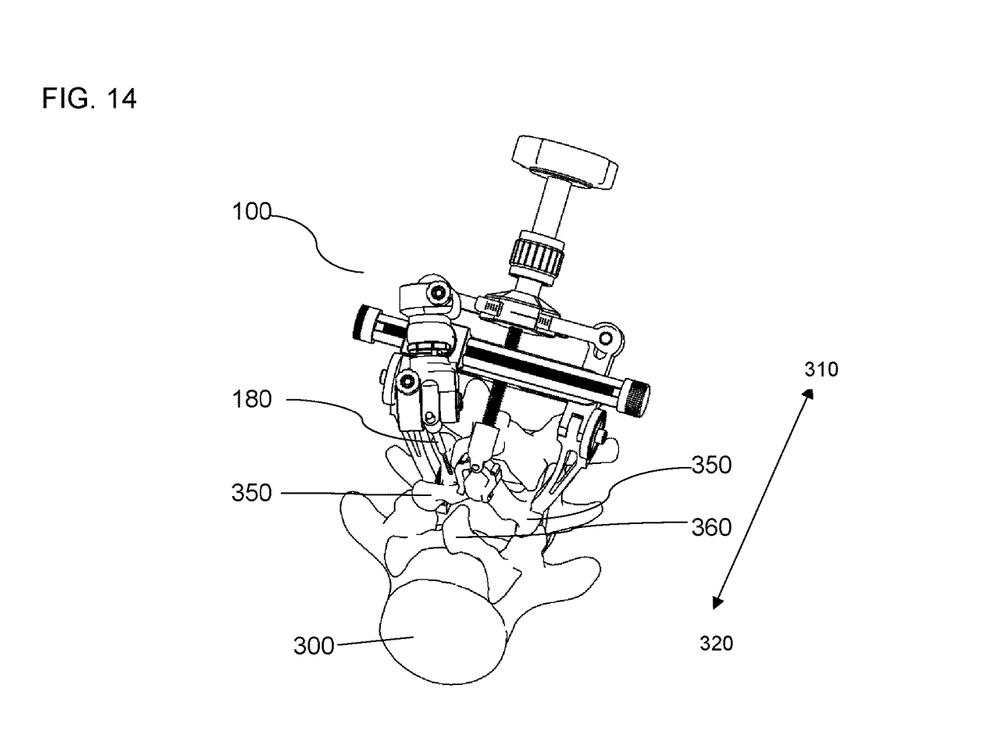
FIG. 14 is a view of apparatus 100 from the inferior toward the superior, showing the three point attachment of 100 to a vertebra and the drill bit oriented in a caudocephalad path sagittally and a laterally directed path in the transverse plane.

In an embodiment, the three-point attachment is supported by a chassis 110 (FIG. 4A). In the embodiment shown in the figures, chassis 110 supports the mandible arms 121 and 122 through mandible support rods 128, which pivot around pivot points 130. Mandible arms 121 and 122 are connected to support rods 128 at pivots 132 and 133. The other end of mandible support rods 128 are connected to rack gears 142 and 144 through pivots 126. Thus, as pivots 126 move towards each other, rods 128 rotate around pivots 130 so that the gap in jaw 120 expands. Conversely, as pivots 126 move apart, rods 128 rotate so that the gap in jaw 120 contracts. During placement of the inventive jig, the gap 120 is adjusted so that the jaws fit into the pars interarticularis 350 of a vertebra (FIG. 14). The gap between the jaws may be adjusted by the surgeon by turning knob 160.

In an embodiment, pivots 126 are connected to rack gears 142 and 144. The surgeon can turn dial 160 which rotates a pinion gear (not shown) in housing 140 that causes the rack gears 142 and 144 to move. Thus, as the surgeon turns knob 160 counterclockwise, pivots 126 will move towards each other, causing the jaw 120 to open (or expand). Conversely, as the surgeon turns knob 160 clockwise, pivots 126 will move apart, causing the gap in jaw 120 to contract.

Figure 10A:
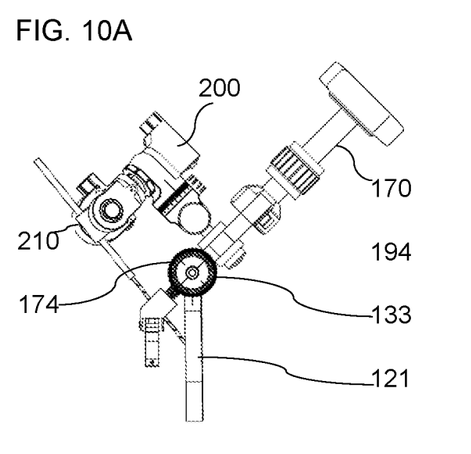
FIG. 10A shows the mandibles in a neutral position at an approximately 135° angle to shaft 170.
Figure 10B:
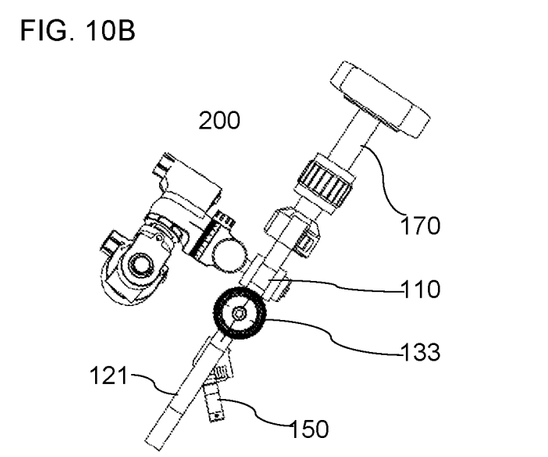
FIG. 10B shows the mandible flexed at a greater angle than 135°.
Figure 10C:
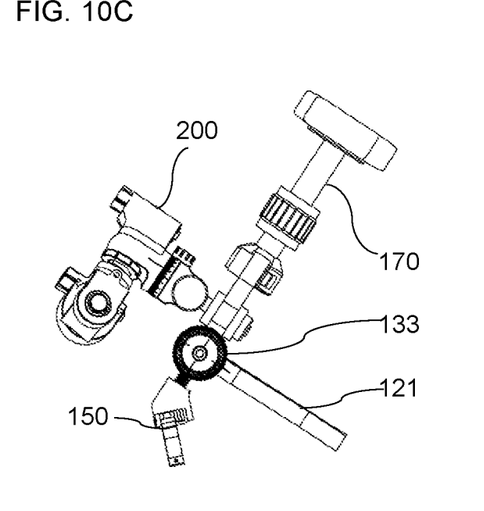
FIG. 10C shows the mandibles flexed at a less than 135° angle to shaft 170.
Figure 11:
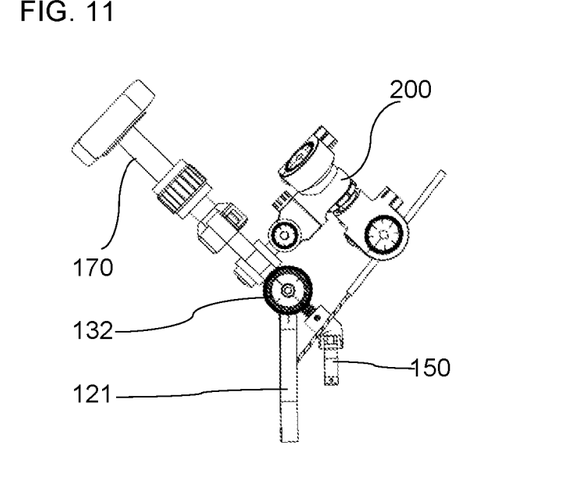
FIG. 11 is an elevation view of the left side of apparatus 100.

In an embodiment, mandible arms 121 and 122 are pivotally affixed to the support rods 128 (one for each mandible arm) though pivot points 132 and 133. Pivots 132 and 133 rotate on an axis that changes the mandible arm angle with respect to a transverse axis of rotation parallel to the chassis (FIGS. 10B and 10C). Pivots 132 and 133 may require a mechanical connection allowing them to be tightened and locked into a desired position.

Figure 5A:
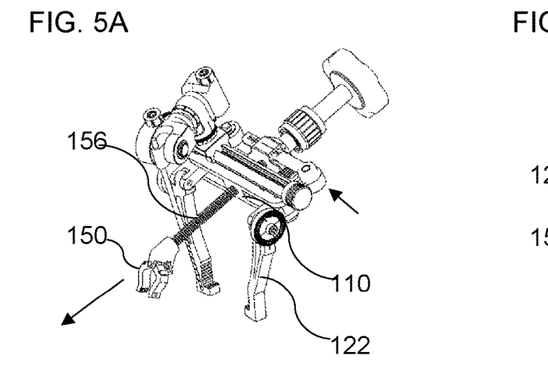
FIG. 5A is a perspective view of the inventive apparatus showing the spinous process clip in an extended position.
Figure 5B:
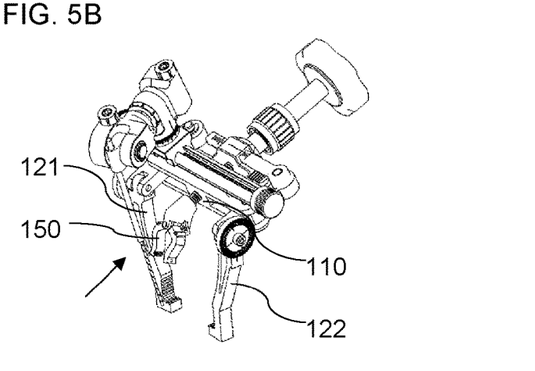
FIG. 5B is a perspective view of the inventive apparatus showing the spinous process clip in a retracted position.

The third attachment point is central clip 150 that contacts the spinous process of the vertebra. In an embodiment, clip 150 is connected to translational screw 156 through elbow 152. Translational screw 156 is controlled by dial 162, so that when the surgeon turns dial 162 clockwise, the clip 150 extends away from chassis 110 on a medial axis (FIG. 5A). When dial 162 is turned counterclockwise, clip 150 retracts, i.e., moves towards chassis 110 (FIG. 5B). Translational screw 156 is supported by chassis 110 through screw hole 164/165. In an embodiment, clip 150 may include spring 154 (FIG. 13) that provides some bias to the two arms of clip 150. In another embodiment, clip 150 may be U shaped or semi-circle shaped to accommodate a contact point on the spinous process which can be then secured with a separate pin or screw.

Thus, all three support points, bilateral jaws 120 and central clip 150 are independently movable to establish a stable support for apparatus 100.

In an embodiment, drill guide support arm 200 is supported on a transverse support that permits the support arm to move laterally as required to guide a drill bit into the correct location. The medial location is determined by the three-point attachment and can be adjusted in particular by changing the angle of the mandible arms around pivots 132 and 133. Moreover, since the placement of screws or guidewires is typically bilateral, the drill guide support arm may have the capability of moving on the transverse support from one side of the vertebra to the other in a lateral direction.

Figure 8:
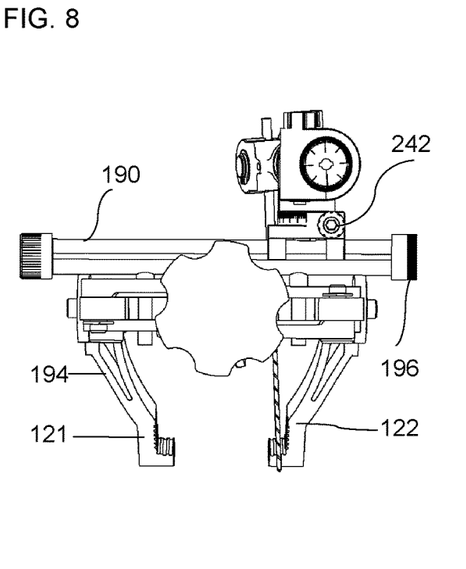
FIG. 8 is an elevation view of the inferior side of the apparatus, looking towards the superior end (head) of the spine.
Figure 9:
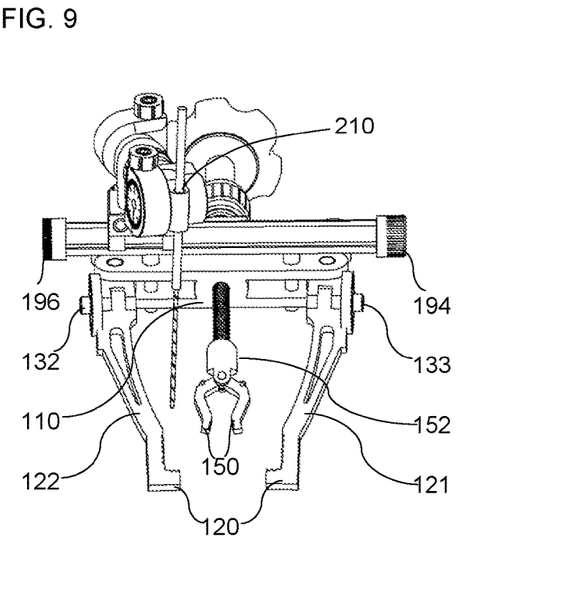
FIG. 9 is an elevation view of the superior side of the apparatus looking in a caudal direction.

In an exemplary embodiment, drill guide support arm 200 is supported on transverse support 190 that is supported by and parallel to chassis 110 (FIGS. 8 and 9). Arm 200 is in contact with housing 191 and translational screw 192, through grooves 252 and female threads 250 respectively.

Figure 3:
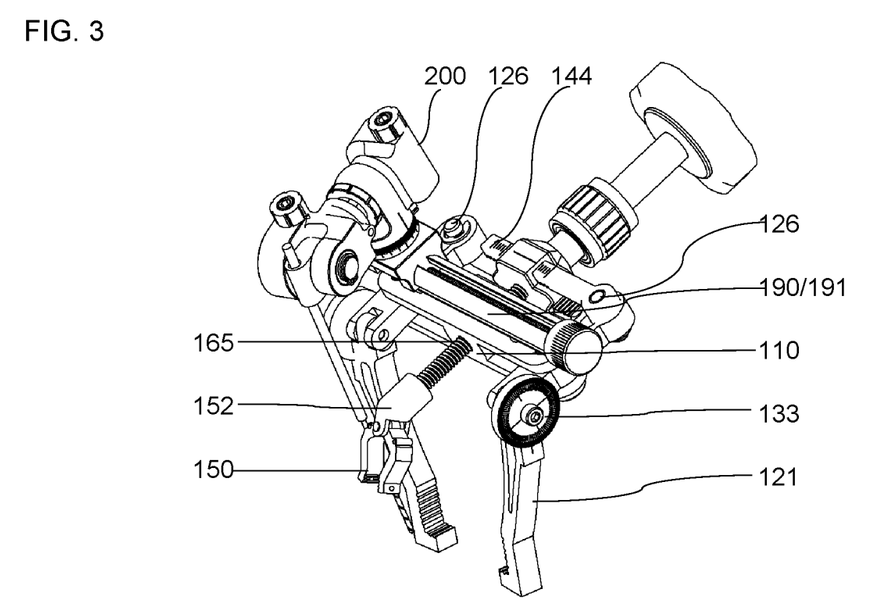
FIG. 3 is an alternative top perspective view of apparatus 100. The cephalad end is the right in the figure, and the caudal end is on the left in the figure.
Figure 5C:
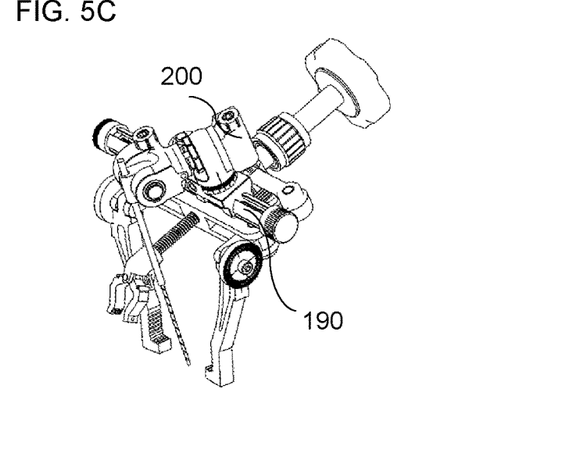
FIG. 5C is a perspective view showing the drill guide support arm moved laterally to the left.
Figure 6:
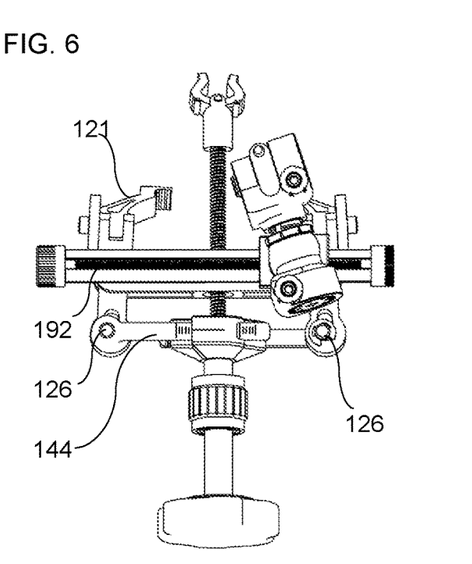
FIG. 6 is an elevation view of the posterior (top) of apparatus 100. The spine would be below the apparatus as shown in FIG. 6.
Figure 7:
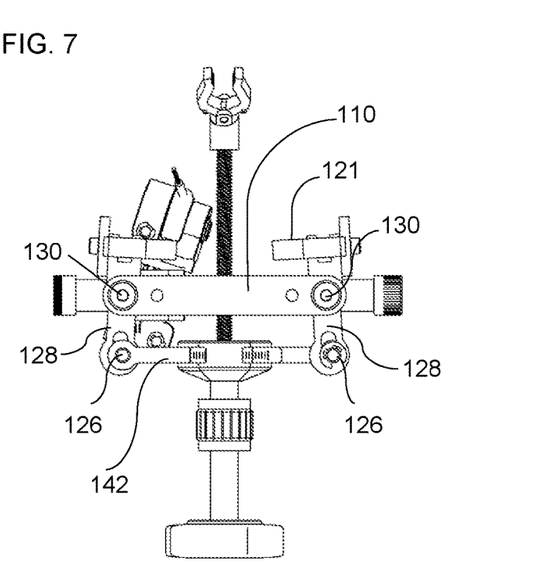
FIG. 7 is an elevation view of the anterior (bottom) side of apparatus 100. This view is from the spine looking away toward the surgeon.

Thus, as translational screw 192 rotates, the entire support arm 200 moves laterally along the transverse translational screw (FIGS. 3 and 5C). In the illustrated embodiment, translational screw 192 is controlled by dial 194. Indicator 196 may show a quantitative measurement of the lateral position of arm 200.

Figure 12C:
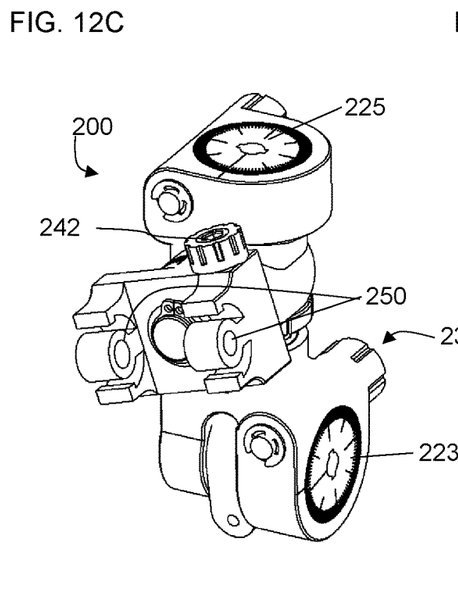
FIG. 12C is an alternative view of the guide support arm.
Figure 13:
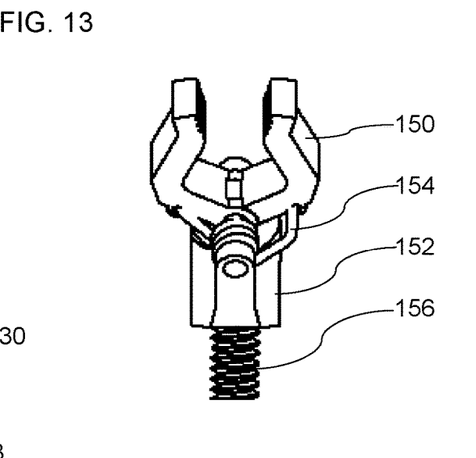
FIG. 13 is a detail of an embodiment of the spinous process clip.

In an embodiment, drill guide support arm 200 has three axes of rotation in order to position drill guide channel 210 in a desired orientation. An exemplary embodiment of the rotational features of arm 200 is illustrated in FIGS. 12A-12C. The x, y, and z axes are shown as 222, 224, and 226 respectively. In the illustrative embodiment, each axis has a keyhole in communication with a worm screw, so that turning the key causes the worm screw to rotate, and the worm screw in turn causes a gear (also termed a worm wheel) to rotate that causes the axis on the arm to rotate. Thus, for the x-axis, keyhole 230 turns worm screw 232 that turns gear 234 to physically rotate the drill guide channel 210 on the x-axis 222 as shown in FIG. 12B. For the y-axis, keyhole 236 turns worm screw 238 that turns gear 240 to physically rotate the drill guide channel 210 on the y-axis 224 as shown in FIG. 12B. For the z-axis, keyhole 242 turns worm screw 244 that turns gear 246 to physically rotate the drill guide channel 210 on the z-axis 226 as shown in FIG. 12B. FIG. 12B is a cutaway view showing the interconnections of the keyholes, worm screws, and worm wheels that rotate each axis of the drill guide support arm 200.

Additionally, each rotational axis in FIGS. 12A-C may have an indicator showing the degree of declination of each axis. Thus, 223 is the indicator for the x-axis, 225 is the indicator for the y-axis, and 227 is the indicator for the z-axis.

As shown in FIG. 12A, there are limits to the declination of each axis. In the illustrated embodiment, the x-axis can rotate 10°, the y-axis can rotate 4°, and the z-axis can rotate 20°.

In an alternative embodiment, the drill guide support arm is movable along a support bar transverse to the spine, and the support arm has pivotal connections that can be tightened, for example with a thumb screw, rather than the worm gear arrangement described above.

In operation, the inventive device 100 uses tripodal support on a single vertebra, as shown in FIG. 14. FIG. 14 depicts a view from the caudal end (320) of the spine, looking towards the cephalad (head) end 310. Legs 121 and 122 are in contact with the pars interarticularis of a vertebra, for example, the L5 vertebra, and clip 150 is grasping the spinous process 360 of the same vertebra. The tripodal support to stabilize the entire apparatus requires the adjustments as discussed above, of the mandible arms and central clip, because there is considerable variation in detailed anatomy from one person to another.

Once the tripodal support is established, drill guide support arm can be positioned in the appropriate lateral position by rotation of the transverse rotational screw 192. The three axes of the drill guide support arm are adjusted as desired and a drill bit 180 is inserted into guide channel 210, and the surgeon is ready to drill.

In an embodiment, various drill sizes may be used, for example, a pilot hole can be drilled with a 1 mm diameter bit, and then a larger hole can be drilled with a 3-4 mm bit. Thereafter screws or guidewires can be inserted that support related hardware for the stabilization and distraction of the spine.

In an embodiment, the tripodal support components may be separate from the translational and drill guide components to allow for a stepwise placement of the entire jig. In this embodiment, the pars and spinous process clamps would first be attached to the vertebrae, then the translational component and drill guide can then be attached to the jig in a separate manual operation to complete the setup. In this embodiment, the drill guide support arm is detachable from the chassis.

In an embodiment, a method of drilling a hole for the placement of screws in a spinal vertebra is provided, using the jig as described above to provide a drill guide and channel for a drill bit to precisely aim a drill bit for drilling in a spinal surgical procedure. In an embodiment, a cortical screw is screwed into the hole thus formed with a screwdriver once the jig and guide are removed. In an embodiment, no tapping or hammering is used in the insertion of the cortical screw; however, once the jig and guide are removed, a tap could then be utilized through the drilled pilot hole.

In an embodiment, the jig of this invention is intended to be reusable, i.e., not single use and not disposable. In an embodiment, the device may be made from a medically compatible metal such as stainless steel or titanium that can be disassembled after use, cleaned, sterilized, reassembled, and reused. The jig should be able to withstand typical temperatures and pressures in a sterilization autoclave.

In an embodiment, the jig is manufactured from a surgical grade steel, such as are austenitic SAE 316 stainless and martensitic SAE 440, SAE 420, and 17-4 stainless steels. SAE 316 and SAE 316L stainless steel is a chromium, nickel, molybdenum alloy of steel that exhibits relatively good strength and corrosion resistance. 316L is the low carbon version of 316 stainless steel. 316L steel in particular is biocompatible when produced to ASTM F138/F139. 316 surgical steel is commonly used in the manufacture and handling of food and pharmaceutical products minimization of metallic contamination is important. The corrosion resistance properties of all stainless steels is greatly enhanced by the passivation process. ASTM A967 details this process.

In an embodiment, the jig is made from a medically compatible tantalum, titanium, tantalum alloy, or titanium alloy. For example, an appropriate titanium alloy may be titanium 6AL4V and 6AL4V ELI (ASTM Standard F1472, https://www.astm.org/Standards/F1472.htm (see also https://en.wikipedia.org/wiki/Ti-6Al-4V)), which are alloys made with about 6% aluminum and 4% vanadium. An appropriate tantalum alloy may be tantalum alloyed with 2.5% to 10% tungsten, or 40% niobium.

A biocompatible lubricant may also be used in the jig to lubricate the moving parts. This may be for example, sterile vegetable oil such as olive oil, ethylene glycol, or Kolliphor® (formerly called Cremophor).

In an embodiment, a method is provided of drilling a hole in a vertebra 300 using the device 100. Also provided is a method of drilling a hole into a vertebra 300 for the placement of a screw or guidewire in a caudal-to-cephalad angle in the sagittal plane and medial-to-lateral in the axial plane 340 where the drill guide channel is adjusted to a position wherein the drill bit guided by the drill guide channel is directed to an entry point 341 medial to the edge of pars interarticularis 350 and directed in a caudal-to-cephalad angle in the sagittal plane and medial-to-lateral in the axial plane, and wherein a hole is drilled by the drill bit. In an embodiment, a cortical screw or guidewire is driven into the hole formed by the drill bit. A screw may be driven with a tap or a screwdriver.

In an embodiment, the drill guide channel may be adjusted to drill a second hole (i.e., a second entry point 341) on the other side of the spinous process 360 from a first entry point 341.

In an embodiment, the parameters for the three-point attachment clamp (pars-to-pars distance, roll back amount from 133 and 132, and spinous process attachment clip) and parameters for the guide support arm (lateral translation on the transverse member, x, y, z axes of orientation) are made from measurements pre-operatively from an imaging study such as a computerized tomography (CT) scan or magnetic resonance imaging (MRI) scan. These parameters comprise seven numbers than guide the placement of the entire jig and serve as a check to make sure the jig is in the correct position, and that the guide channel is in the correct orientation. For example, the workflow for establishing the correct configuration of the jig may involve:

(a) First obtaining a pre-operative CT or other advanced scan and importing the image data into appropriate 3-D software.

(b) The surgeon would then place virtual screws at desired locations in the 3D software, and the software would then extrapolate the trajectory and position of the drill guide channel and place a virtual jig on the vertebral body at three known points (both pars and a point on the spinous process). The software would then determine the seven numbers/parameters (three for the clamp and four for the guide arm). These parameters are: (1) pars-to-pars distance (i.e., expansion and contraction of the mandible jaws to fit into the pars of the particular vertebra of the particular patient), (2) extension of spinous process at point of attachment, (3) pivot angle (how many degrees to roll the jig rostrally around the transverse pivots on each mandible arm). These first three parameters establish the stable three-point attachment of the jig to a vertebra. The next parameters are (4) medial-lateral translation of the drill guide arm on the chassis, and (5), (6), and (7), and three degrees of freedom for the drill guide/barrel on the drill guide arm that allows the barrel to swivel in the x, y, and z planes. These seven parameters are unique to each surgical vertebra.

In an exemplary surgery for drilling holes in the L3-L4 vertebrae, the surgeon makes a dissection to expose the L3 pars, L3 spinous process, L4 pars, and L4 spinous process. The surgeon may then use fluoroscopic imaging to identify the correct level of surgery. The surgeon would then instruct a technician in the operating room to set the correct parameters for the clamp on the jig and the technician would then hand the clamp to the surgeon for placement on the correct vertebra. The surgeon would then make adjustments to obtain a firm attachment of the clamp into position. In an embodiment, a safety check is provided as a stop on the knob 160 that prevents the surgeon from over or under-tighten the knob. This is because the stop on knob 160 is a hard stop that lets the surgeon know the jig is sitting where the software extrapolation determined it to sit. If the jig is incorrectly positioned, the hard stop would kick in and the clamp will either be too loose, or the surgeon won't be able to reach the hard stop indicator at all. Either way, the clamp won't be seated properly and that will be apparent to the surgeon.

Once the clamp is in position, the guide arm 200 would be clipped on to the transverse member of the chassis. The three axes (x, y, and z rotation) may be pre-set. Once the guide is on the clamp, the jig is now complete. The surgeon would then turn the medial-lateral dial as the seventh parameter based to the left side, and then drop a pre-set drill bit through the guide/barrel. On confirmation of the correct entry point and trajactory, the hole would be drilled. In most procedures, bilateral screws are needed, so the surgeon would then turn the medial-lateral dial to move the guide arm to the right side. The x, y, and z axes on the drill bit would be changed as required for the other side of the vertebra, and the surgeon would drill the second hole. Now we have the trajectories drilled. The jig apparatus would be then loosened by turning the knob 160 and removed, and the surgeon would then tap and place the screws or drive screws with a screwdriver.

The process would be repeated for any additional vertebrae requiring screws, for example the L3 vertebra. The technician would set the three clamp parameters, and hand the clamp to the surgeon, who would attach the clamp to the L3 vertebra as before. The guide arm would be attached, positioned on the left, and the four parameters would be confirmed and adjusted as before. The left hole would be drilled. The guide arm would then be repositioned on the right side and the three axes on the guide arm would be adjusted as needed, and the second hole in that vertebra would be drilled. The jig apparatus would be then loosened by turning the knob 160 and removed. When the drilling is complete, the apparatus would be given to the technician for disassembly, cleaning, and sterilization for re-use.

The use of the inventive jig is not limited to any particular vertebra and can be used on any location on the spine.

Drawing legend

| No. | Description |
|---|---|
| 100 | apparatus for use by a surgeon in spinal surgery adapted to guide the placement of a drill bit |
| 110 | chassis |
| 120 | jaw that contacts the pars interarticularis |
| 121 | Left jaw (left mandible) |
| 122 | Right jaw (right jaw) |
| 126 | Rack pivot - pivot connecting rack gears 142/144 and mandible arm 128 (bilateral) |
| 128 | Mandible (Jaw) support rods (bilateral) |
| 130 | Mandible support arm pivot |
| 132 | Right mandible transverse pivot |
| 133 | Left mandible transverse pivot |
| 140 | Gear housing containing pinion gear controlling expansion and contraction of pars interarticularis jaws |
| 142 | Upper rack gear |
| 144 | Lower rack gear |
| 150 | Spinous process clip |
| 152 | Clip support bracket (elbow) |
| 154 | Spring on clip |
| 156 | medial translational screw controlling extension and retraction spinous process clip |
| 160 | Knob controlling the gap in the pars interarticularis jaws |
| 162 | Rotatable grip adjusted spinous process clip extension and retraction |
| 164 | Female screw hole in support bracket for inner shaft 174 (superior view) |
| 165 | Female screw hole in support bracket for inner shaft 174 (inferior view) |
| 170 | Double shaft controlling jaw gap and extension of clip 150 |
| 180 | Drill bit |
| 190 | Transverse support assembly |
| 191 | Transverse support assembly housing |
| 192 | lateral translational screw on a medio-lateral axis |
| 194 | lateral translational screw thumb dial |
| 196 | lateral translational screw indicator |
| 200 | Drill Guide support arm |
| 210 | Drill guide channel (barrel) |
| 220 | Axis of lateral movement of Drill Guide support arm |
| 222 | X axis of Drill Guide support arm |
| 223 | Indicator of degree of declination for x-axis |
| 224 | Y axis of Drill Guide support arm |
| 225 | Indicator of degree of declination for x-axis |
| 226 | Z axis of Drill Guide support arm |
| 227 | Indicator of degree of declination for x-axis |
| 230 | Keyhole to rotate Drill Guide support arm on x axis |
| 232 | Worm screw that rotates Drill Guide support arm on x axis |
| 234 | Gear for x axis rotation |
| 236 | Keyhole for y axis rotation |
| 238 | Worm screw for y axis rotation |

-continued

Drawing legend

| No. | Description |
|---|---|
| 240 | Gear for y axis rotation |
| 242 | Keyhole for z axis rotation |
| 244 | Worm screw for z axis rotation |
| 246 | Gear for z axis rotation |
| 250 | Female thread on arm 200 for translational screw (bilateral) |
| 252 | Grooves on arm 200 that contact housing 191 |
| 300 | Vertebra - this can be any vertebra on the spine. |
| 310 | Cephalod (Superior) orientation of spine |
| 320 | Caudal Inferior orientation of spine |
| 330 | "traditional" pedicle screw trajectory |
| 340 | caudocephalad path sagittally and a laterally directed path in the transverse plane screw trajectory |
| 341 | caudocephalad path sagittally and a laterally directed path in the transverse plane screw entry point |
| 350 | Pars interaticularis |
| 360 | Spinous process of a vertebra |

The invention claimed is:

1. A device for use by a surgeon in spinal surgery adapted to guide the placement of a drill bit for the insertion of screws or guidewires in the spine of a patient in need of spinal fusion, comprising
   a. a chassis having a three-point attachment configured to be attached to a vertebra comprising two mandibles that form a jaw configured to contact the pars interarticularis of a vertebra, and a central attachment clip adapted to contact the spinous process of the same vertebra, so that the two jaws and central attachment clip form a stable three-point attachment to the vertebra;
   b. wherein the chassis has a transverse member and a drill guide support arm comprising a drill guide channel is moveable on the transverse member and is movable laterally from one side of the chassis to the other and is securable into a desired lateral position;
   c. wherein the guide support arm has three axes of rotation to position the drill guide channel in a desired position and orientation, and wherein the channel determines the trajectory for a drill bit inserted through the guide channel; and
   d. wherein the drill guide channel is used to guide a drill bit to drill a hole for a spine screw or guidewire in a vertebra.

2. The device of claim 1, wherein the two mandibles that form a jaw configured to contact the pars interarticularis of a vertebra pivot on a transverse axis.

3. The device of claim 1, wherein the two mandibles that form a jaw configured to contact the pars interarticularis of a vertebra move such that the gap in the jaw can expand and contract.

4. The device of claim 1, wherein the central attachment clip adapted to contact the spinous process of the same vertebra extends and retracts relative to the chassis.

5. A device for use by a surgeon in spinal surgery adapted to guide the placement of a drill bit for the insertion of screws or guidewires in the spine of a patient in need of spinal fusion, comprising
   a. a three-point attachment configured to be attached to a vertebra comprising two mandible arms that form a jaw configured to contact the pars interarticularis of a vertebra where screws are to be inserted, and a central clip adapted to contact the spinous process of the same vertebra;
   b. wherein each mandible arm and the central clip are connected to a chassis, such that the jaw formed by the mandible arms can expand or contract to make a firm connection with the pars interarticularis and the central clip can extend or retract to make a firm connection to the spinous process, such that a stable three-point attachment of the chassis to the vertebra is made;
   c. wherein the chassis, when stabilized in position, is transverse to the spine;
   d. wherein a drill guide support arm comprising a drill guide channel is moveable on a transverse support assembly connected to the chassis and can move transversely on a medio-lateral axis from one side of the transverse support assembly to the other and is securable into a desired lateral position;
   e. wherein the guide support arm has three perpendicular axes of rotation to position the drill guide channel in a desired position and orientation, wherein a drill bit can be inserted into the drill guide channel, the channel determines the placement and trajectory for the drill bit; and
   f. wherein the drill guide channel is used to guide a drill bit to drill a hole for a spine screw or guidewire.

6. The device of claim 5, wherein the transverse support assembly further comprises a lateral translational screw on a medio-lateral axis, wherein the lateral translational screw supports the drill guide support arm, and wherein the lateral translational screw can be rotated by a dial to position the drill guide support arm in a desired lateral position.

7. The device of claim 5, wherein the drill guide support arm comprises three worm screws and gears that control the x, y, and z axes of the drill guide support arm.

8. The device of claim 1, wherein the drill guide support arm is detachable from the chassis, and wherein the drill guide support arm is attachable to the chassis.

9. The device of claim 5, wherein the drill guide support arm is detachable from the transverse support assembly and wherein the drill guide support arm is attachable to the transverse support assembly.

10. The device of claim 5, wherein the central clip is moveable along a medial axis and can extend or retract in a perpendicular axis to the transverse support assembly.

11. The device of claim 5, wherein the central clip is mounted on a medial translational screw threaded through a female fitting in the chassis, and the rotation of the medial translational screw extends or retracts the central clip relative to the position of the transverse support assembly.

12. The device of claim 11, wherein a dial is used by the surgeon to rotate the medial translational screw.

13. The device of claim 5, wherein each arm that forms a jaw mandible independently rotates on a transverse axis through a pivot point for each arm.

14. The device of claim 5, wherein each arm that forms a jaw mandible rotates on a medial axis in coordination, such that the jaw mandible moves between an expanded and contracted position.

15. The device of claim 14, wherein the coordinated movement of the jaws between expanded and contracted positions is controlled by a rack and pinion screw, wherein a jaw pinion screw moves an upper and lower rack that are each in communication with a rack pivot and mandible support lever, such that as the jaw pinion screw rotates, the rack pivots move together or farther apart and the mandible support levers move the mandible on a medial axis to expand or contract the gap at the end of the jaw.

16. The device of claim 1, wherein the drill guide channel is adjusted to a position wherein the drill bit guided by the drill guide channel makes a drilled hole at an entry point medial to the edge of pars interarticularis and directed in a caudal-to-cephalad angle in the sagittal plane and medial-to-lateral in the axial plane.

17. The device of claim 1, wherein the spine screw or guidewire is used for a spinal fusion procedure.

18. The device of claim 1, wherein the spine screw or guidewire is used for a cervical, thoracic, lumbar, or sacral spinal fusion procedure or a combination thereof.

19. The device of claim 1, made from a surgically compatible metal that can be sterilized, wherein the metal is selected from stainless steel, titanium or a titanium alloy, and tantalum or a tantalum alloy.

20. The device of claim 1, wherein the device is sterilizable and reusable.

* * * * *